United States Patent [19]
Bell

[11] Patent Number: 5,997,504
[45] Date of Patent: Dec. 7, 1999

[54] NEEDLE REMOVAL AND CONTAINMENT DEVICE AND METHOD OF USING SAME

[75] Inventor: Craig J. Bell, Swanzey, N.H.

[73] Assignee: Medcare Medical Group, Inc., E. Swanzey, N.H.

[21] Appl. No.: 09/256,155

[22] Filed: Feb. 24, 1999

Related U.S. Application Data

[63] Continuation-in-part of application No. 08/910,928, Aug. 8, 1997, Pat. No. 5,879,330.

[51] Int. Cl.$^6$ ....................................................... A61M 5/32
[52] U.S. Cl. ............................................. 604/93; 604/500
[58] Field of Search ............................. 604/93, 500, 508, 604/511, 175, 164, 165, 171, 177, 198, 115, 116, 117; 128/919

[56] References Cited

U.S. PATENT DOCUMENTS

| | | | |
|---|---|---|---|
| 4,581,020 | 4/1986 | Mittleman | 604/175 |
| 5,135,502 | 8/1992 | Koenig, Jr. et al. | |
| 5,248,301 | 9/1993 | Koenig, Jr. et al. | |
| 5,460,612 | 10/1995 | Madore | 604/116 |
| 5,571,092 | 11/1996 | Thompson | 128/919 X |
| 5,709,660 | 1/1998 | Doyle | 604/117 X |
| 5,879,330 | 3/1999 | Bell | 604/93 |

*Primary Examiner*—John D. Yasko
*Attorney, Agent, or Firm*—Davis and Bujold

[57] ABSTRACT

A needle retraction device for removing a needle from a patient. The needle retraction device comprising a housing having an exterior wall which defines an interior compartment. A moveable member, having a pair of spaced apart movable legs or shoulders, separated from one another by an elongate slot, is located within the interior compartment. The pair of spaced apart movable legs or shoulders are also spaced from a remainder of the moveable member by a cavity or area which is sized to receive a coupling hub of a needle therein. The moveable member is movable from a first position, in which the pair of spaced apart movable legs or shoulders are located outside of the interior compartment of the needle retraction device for receiving a needle, and a second retracted position, in which the pair of spaced apart movable legs or shoulders, along with a supported needle or needle assembly, are completely retracted inside the interior compartment of the housing to prevent an inadvertent needle stick.

19 Claims, 16 Drawing Sheets

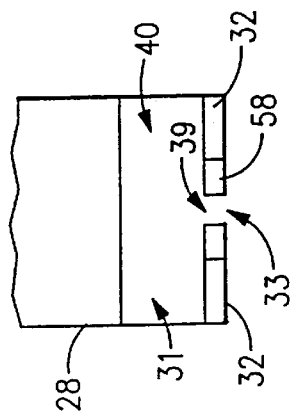
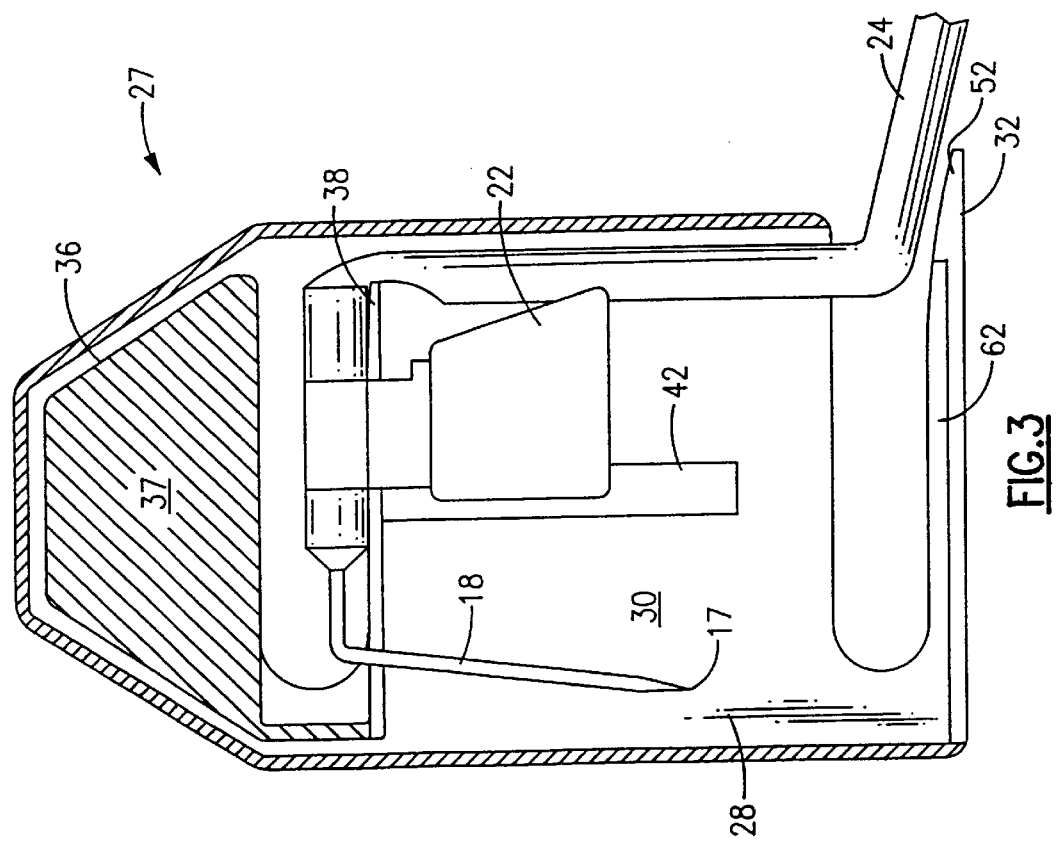

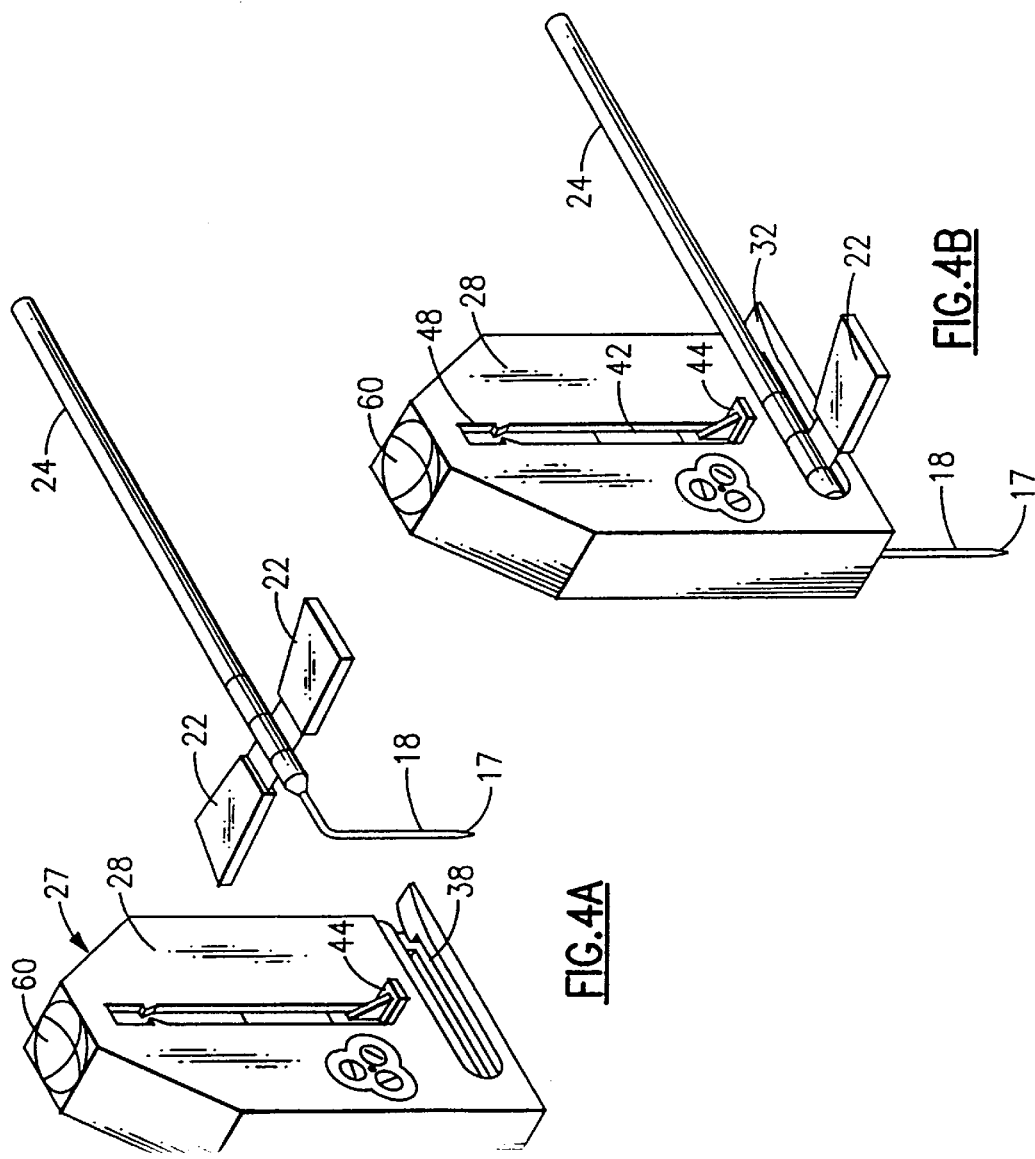

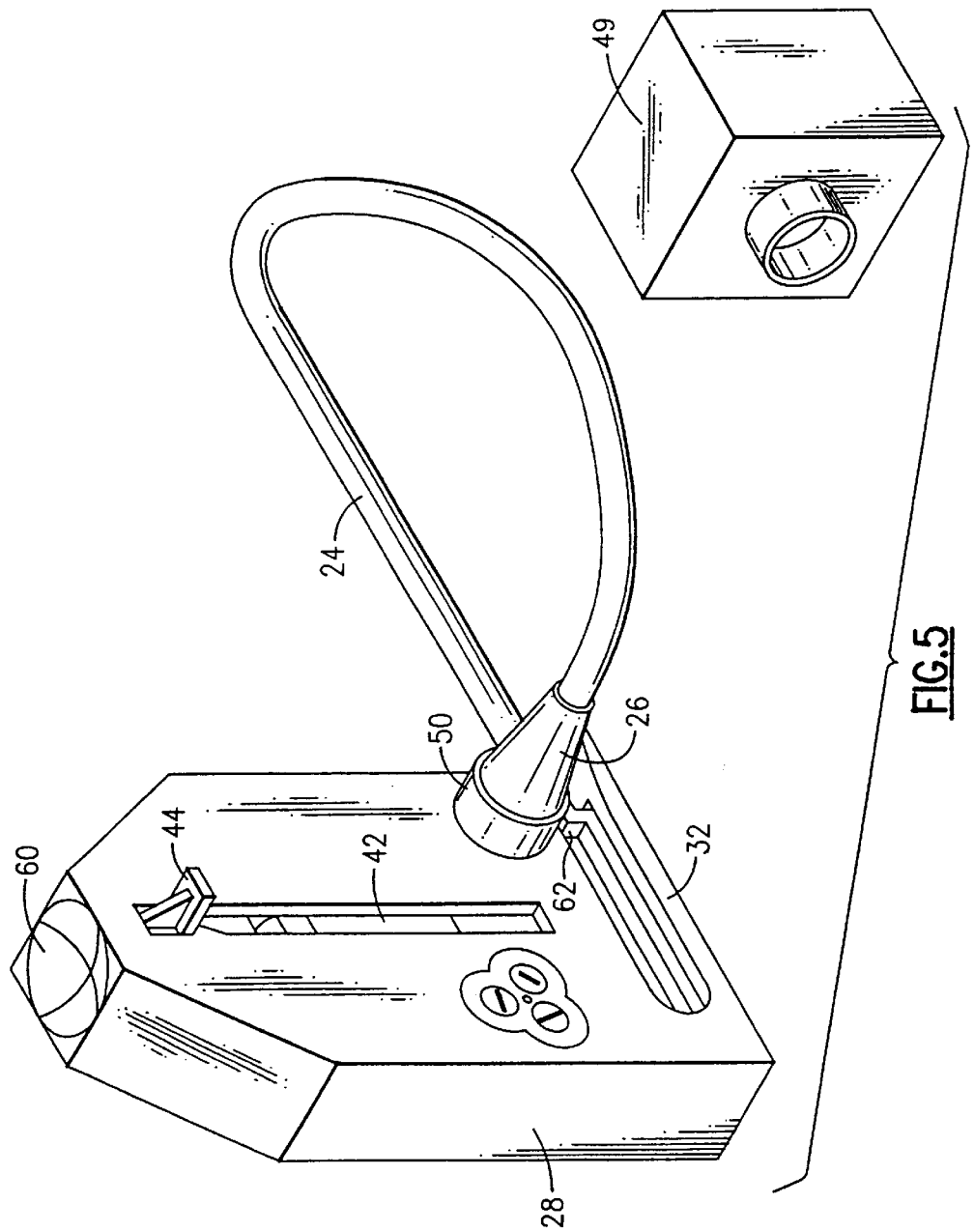

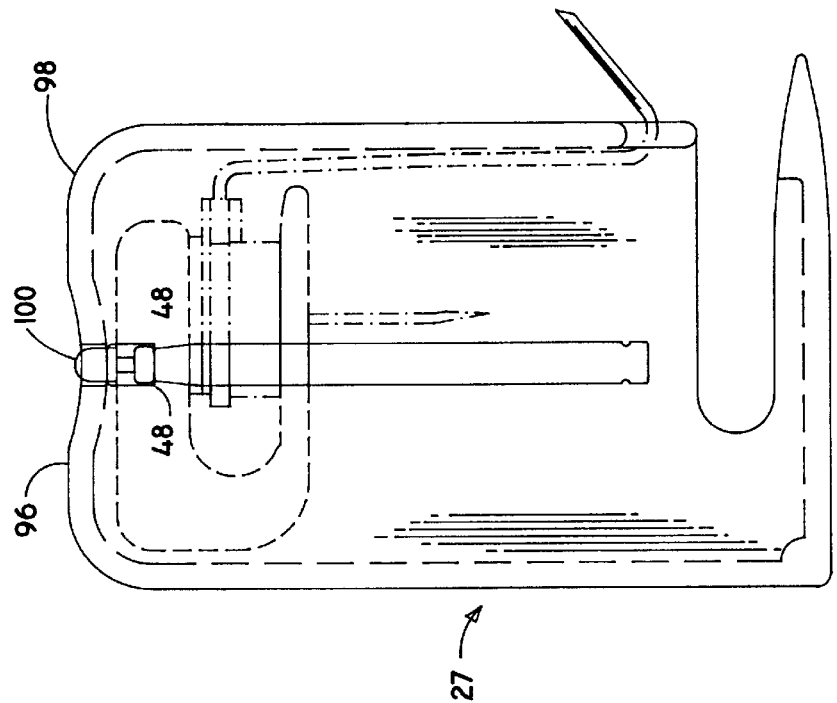
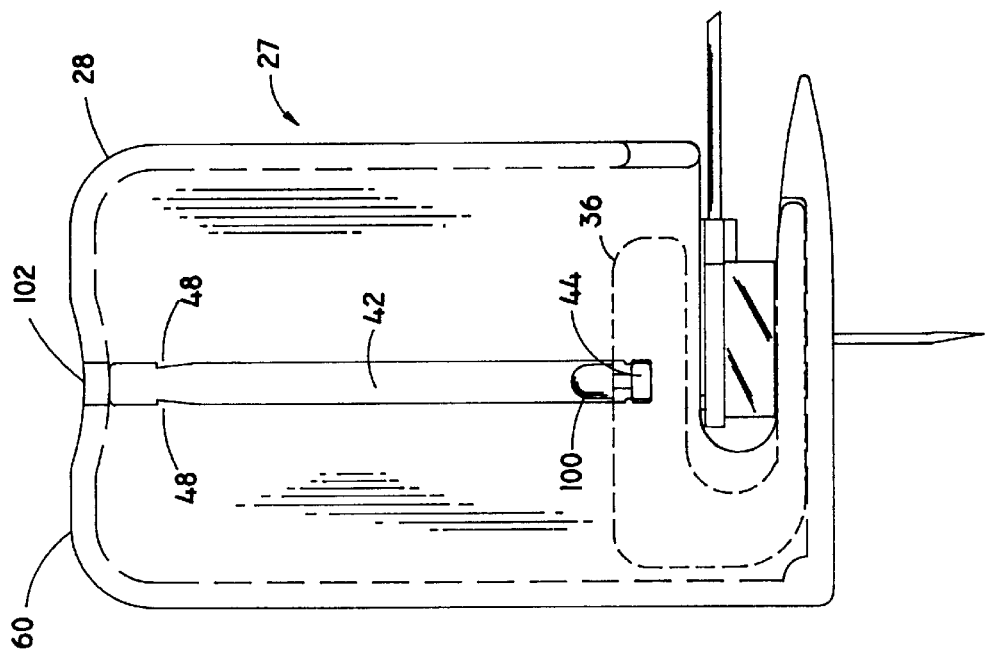

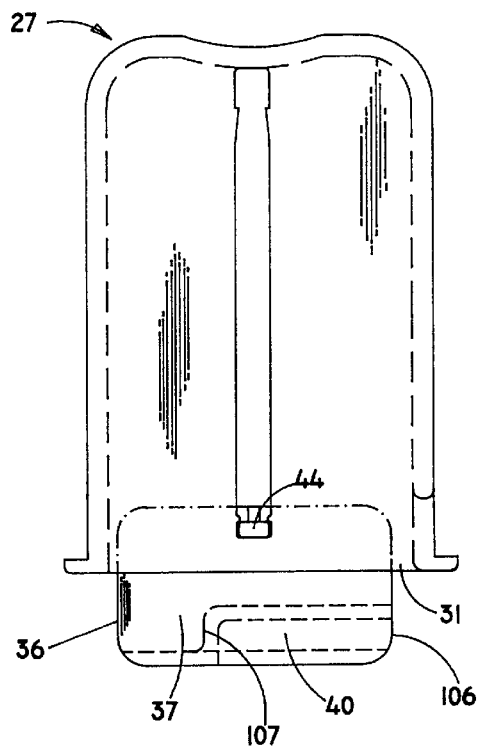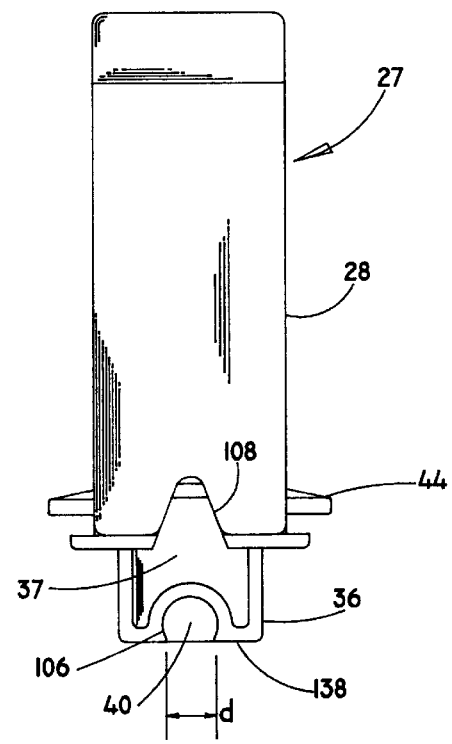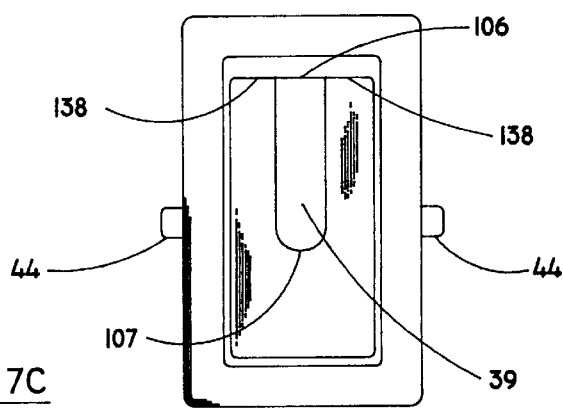

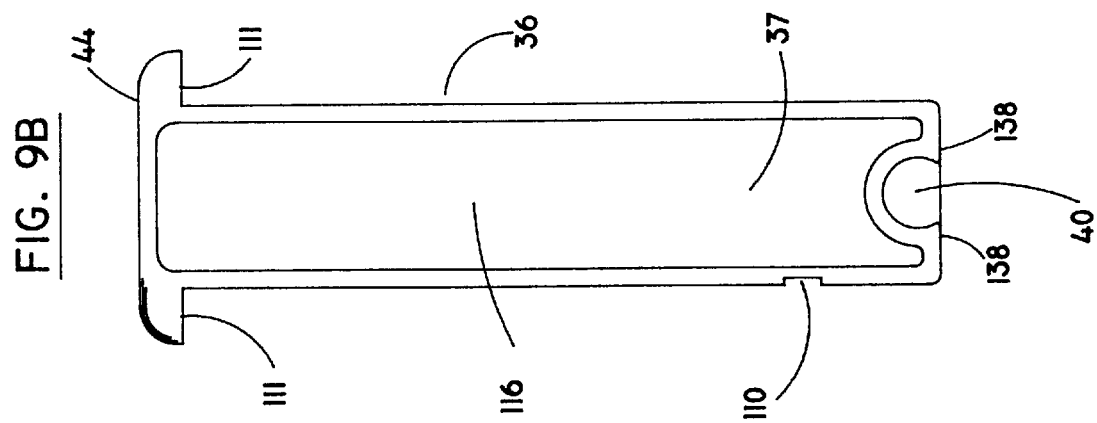
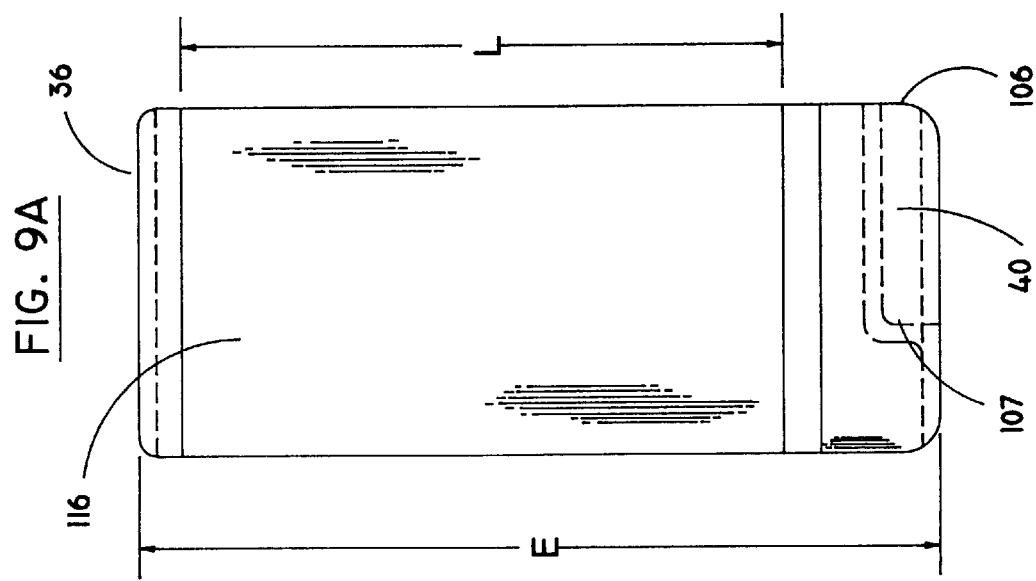

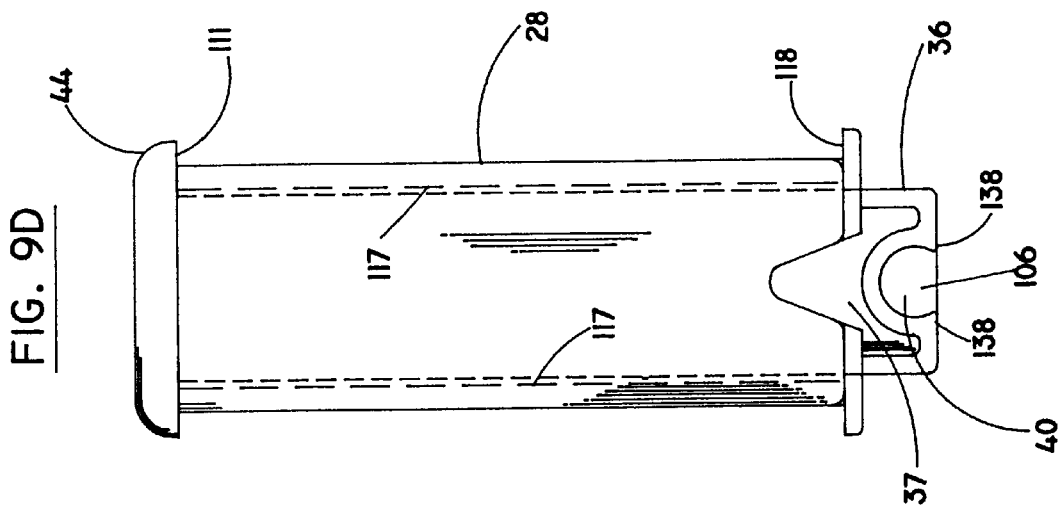
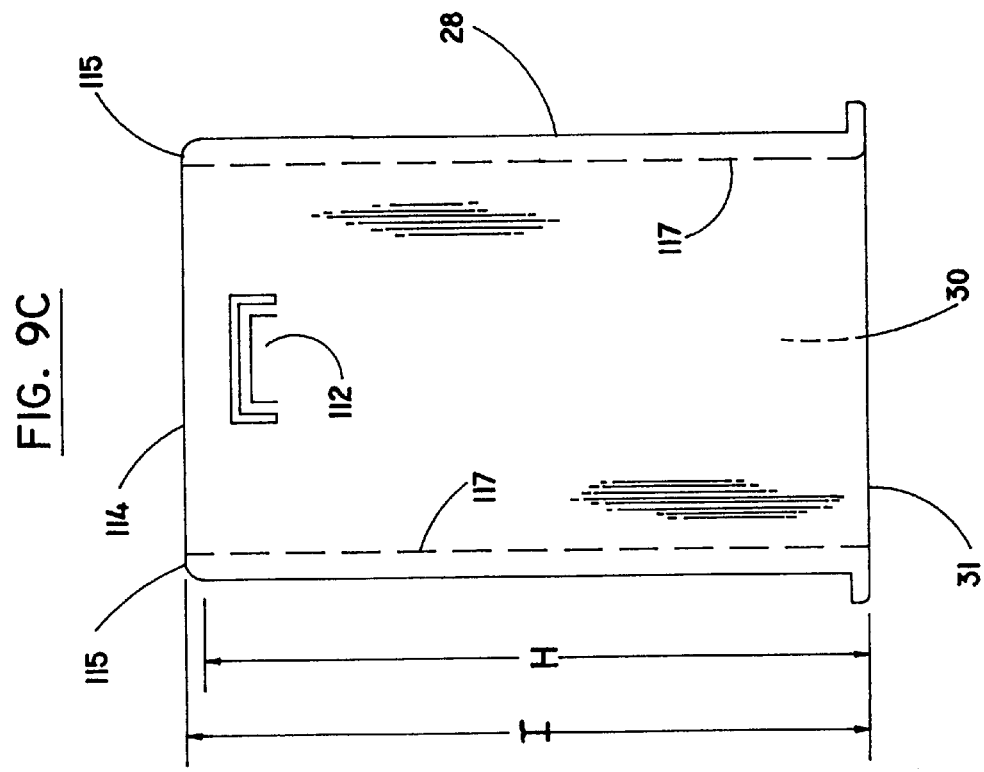

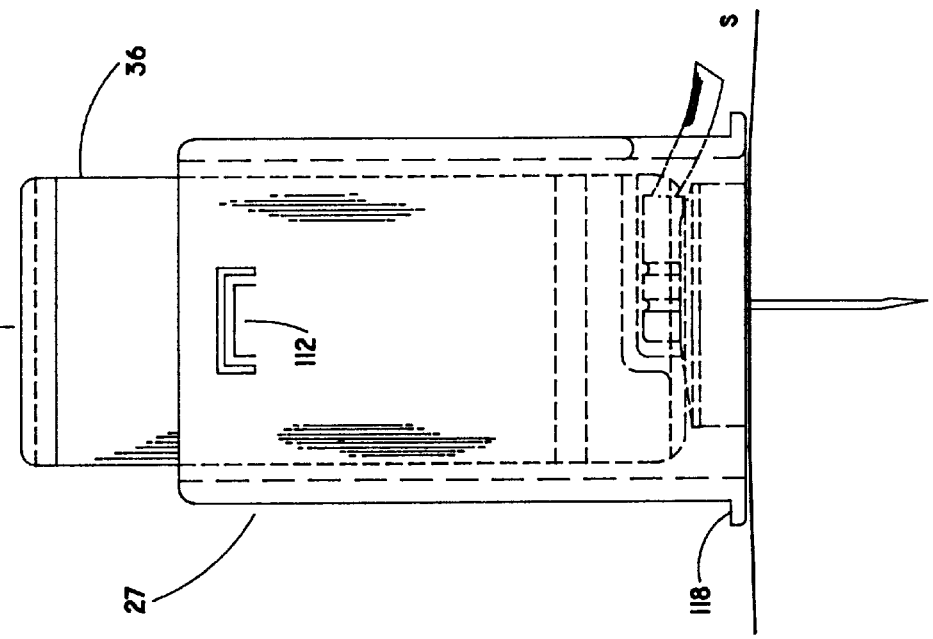
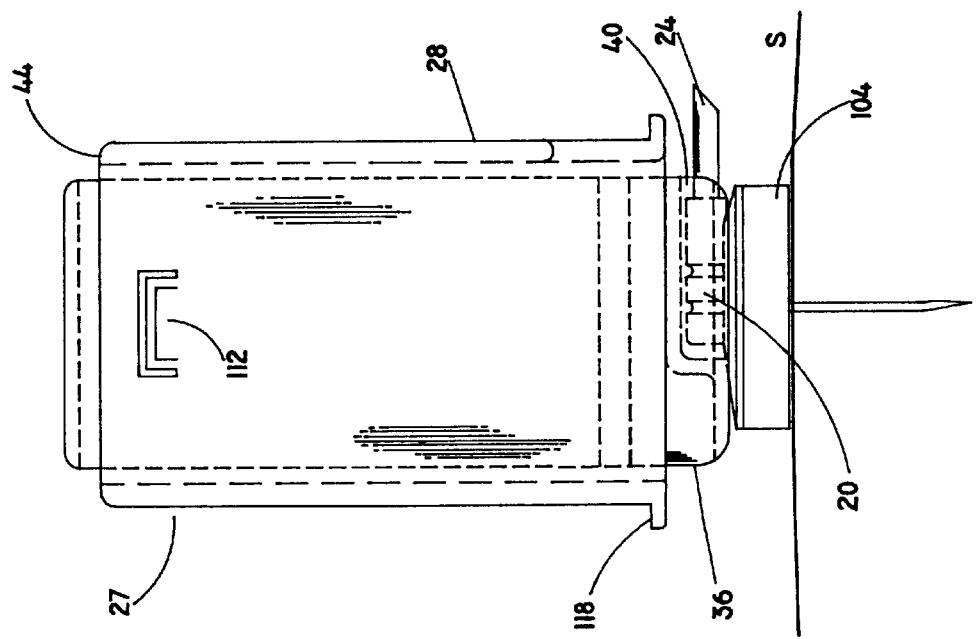

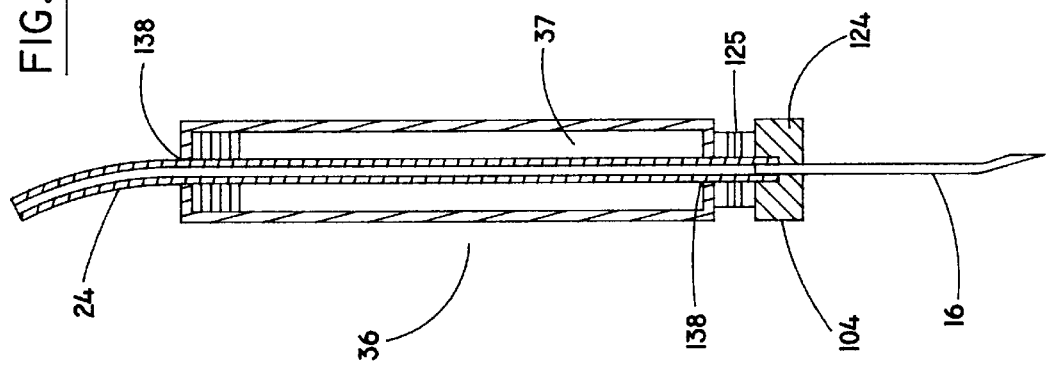
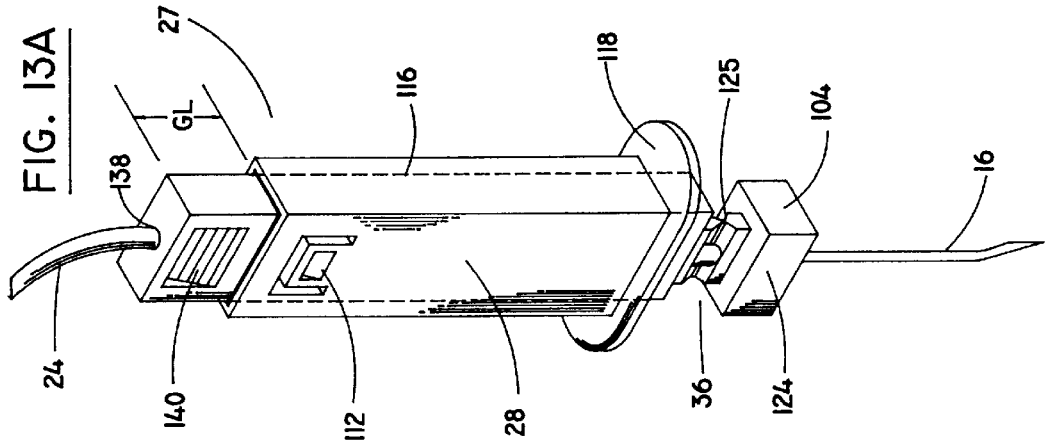

NEEDLE REMOVAL AND CONTAINMENT DEVICE AND METHOD OF USING SAME

This application is a continuation-in-part of Ser. No. 08/910,928 filed Aug. 8, 1997 now U.S. Pat. No. 5,879,330.

FIELD OF THE INVENTION

The present device relates to a new medical device that allows for the safe removal and containment of a needle, such as a Huber angled needle, from a vascular access port implanted subcutaneously in the chest or other area of a patient.

BACKGROUND OF THE INVENTION

The risk of cross-contamination and infection from needle sticks are well documented in the associated literature. These include the contraction of life threatening HIV virus, several strains of hepatitis and other blood and body fluid borne diseases.

Surgically implanted vascular access ports have been used by the medical community for many years. They are a means of allowing for the easy removal of blood for laboratory testing along with providing for the repeated infusion of medication with as little discomfort to the patient as possible. These ports are placed in the chest of the patient, with a catheter extending into a blood vessel.

The port is typically constructed of biocompatible metal with a thick elastomeric membrane septum that is positioned under the surface of the skin, but accessible to needle penetration. The septum makes it possible for a needle to penetrate the port to an inner septum chamber for the infusion of a drug through the needle into the port, followed by the needle's removal without leakage from the port. The purpose of the port is to allow for easy drug delivery without excess needle sticks to the patient, however, the thickness of the port's septum increases the potential of an inadvertent needle stick to the patient or care giver during the withdrawal of the needle from the port.

The type of needles used with the vascular ports are termed "Huber" angled needles. These needles are unique in that they contain a ninety degree bend halfway along the needle shaft and include handling/securing wings located immediately adjacent the bend. The bend in the needle shaft allows the handling/securing wings to be secured to the skin of the patient with tape while the port is in use.

Additionally, these needles can be attached to a coupling hub that is either integral with a base or supported by a base forming a needle assembly. In this configuration with the Huber needle engaged in the port, the supporting base rest on the patient's skin. This base can be provided with foam cushioning and a bottom adhesive surface for added comfort and stability. One such Huber needle assembly having those above mentioned features is "The Gripper(™)" from SIMS Deltec of St. Paul, Minn.

The Huber needles are noncoring, which means that they are able to penetrate cleanly into the vascular port, much like a knife, but upon removal from the port, the port's septum closes completely. This is a very important feature with regard to leakage from the septum and also allows the septum to be accessed well over 1,000 times without damage to the septum.

To remove the needle from the septum, the care giver typically places his/her first and middle fingers on the port to support it. The fingers must be positioned on each side of the needle shaft to properly support the needle. Downward pressure must be supplied by the fingers during the needle's removal to stabilize the port. Care must be given, because excess drag from the needle's removal can cause the implanted catheter to disconnect from the port or pull the catheter out of the vessel. The other hand is used to remove the needle by grasping its handling/securing wings and using considerable upward force to remove the needle from the patient. The care giver, when removing the needle, may inadvertently counter this force by thrusting the needle back in the direction of the port toward the hand stabilizing the port, which can lead to a needle stick to either the patient or the care giver.

The earlier references disclose several attempts at addressing the needle stick problem. However, none of the proposed solutions are user friendly or low in cost. For example, the Madore device, U.S. Pat. No. 5,460,612, discloses a device with two convex shaped prongs arranged in a "V" shape that are attached to a handle. With this device, the needle must be carried to a sharps disposal device with the potential for needle sticks occurring during the needle's placement in the device. In addition, the Madore device is preferably made of stainless steel, which would necessitate its resterilization between use, making the device labor intensive and expensive.

The Thompson device, U.S. Pat. No. 5,571,092, discloses a cylindrical shaped hollow bodied device that is open with flaps, at one end, and contains a slot in the other, where the tips of a hemostat are placed through the slot to grasp and remove the needle. Upon grasping the needle with the hemostat tips, downward pressure is placed on the top of the cylinder, the needle is forced upward into the hollow body with the flaps preventing the needle from leaving the container. The Thompson device is awkward to use, the hemostat is difficult to manipulate through the slot in the top of the container and the device is relatively expensive.

The Doyle Extractor, by Safetech International, Inc. (U.S. Pat. No. 5,709,660), is a device that utilizes a disposable reverse hemostat type design, with the tips apart when the handles are together. The tips have slots in them to accommodate the needle. This device does not address the problem of needle containment once the needle is removed or the possibility of inadvertent needle sticks. Also, the potential for blood aerosol occurring is increased.

Although previous devices have attempted to accommodate all potential problems that can occur with the use of the Huber needles with vascular ports, improvements are still necessary. As the number of blood-borne diseases increases, the safety of all concerned increases. A device that is both cost effective and safe to both the patient and care giver is needed in the health-care industry of today.

SUMMARY OF THE INVENTION

Wherefore, it is an object of the present invention to overcome the aforementioned problems and drawbacks associated with the prior art designs.

An object of the present invention is to generally provide a medical device and a method that allows for the use and safe removal and containment of a needle or needle assembly from a vascular access port implanted subcutaneously in the chest of a patient.

Another object of the invention is to provide complete retraction of a needle or needle assembly, used in combination with a vascular port, via a pair of movable legs or shoulders into a protective exterior housing to prevent inadvertent needle stick to a patient, a care giver as well as another individual.

A further object of the invention is to provide an inner movable or slide member, supporting a pair of movable legs or shoulders, with an indicator button which is aligned to mate with a button hole, provided in the exterior housing, to produce a positive indication of when the slide member is moved to its fully retracted position.

Yet another object of the present invention is to provide the exterior housing, with a through bore extending therethrough, and to provide the movable or slide member as a completely separate component, from the exterior housing, but the movable or slide member has a sufficient long length so that the slide member can extend project through the through bore so that a needle retraction recessed, supported by the slide member, is located outside the housing for engagement with a desired needle or needle assembly to be removed.

A further object of the invention is to provide one end of the inner slide member with a needle retraction cavity which is sized to intimately engage a hub housing of a needle assembly to facilitate removal of the needle assembly.

Another object of the invention is to provide the needle assembly with a pair of guide tabs which are permanently connected to the needle assembly, via a living hinge, which facilitates a pivoting motion of the guide tabs from a supine position to facilitate utilization of the device and an upright position which facilitates removal of the needle assembly.

Still another object of the invention is to provide a sleek and compact exterior housing which is able to pivot from a supine position to an upright position, and vice versa, to facilitate ease of use and removal of the needle assembly.

A further object of the present invention is to minimize the size of slots or openings provided side walls of the in the exterior housing, or eliminate them in their entirety, to minimize the possibility of an inadvertent needle stick to a patient, care giver as well as another individual.

Yet another object of the invention is to enclose the coupling of the tubular extension to the needle, within the inner slide member, to further streamline the size and appearance of the device according to the present invention.

It is not intended that the device or the method be limited in any way to the types of materials used in the construction of the angled needle removing device, nor to its shape, size or number of parts. It is contemplated that a needle be angled in the range of about 0° to about −180° and that more than one needle per device can be accommodated at any one time.

DESCRIPTION OF THE FIGURES

The invention will now be described, by way of example, with reference to the accompanying drawings in which:

FIG. 2C is a partial diagrammatic side elevated view of the device according to the present invention;

FIG. 3 illustrates a diagrammatic cross-sectional view of the device, according to the present invention, in the second locked position supporting and encasing a Huber needle;

FIG. 4A illustrates a diagrammatic perspective view of the device, according to the present invention, shown separately from a Huber angled needle;

FIG. 4B illustrates a diagrammatic perspective view of the device, according to the present invention, showing its initial engaged position with the Huber angled needle;

FIG. 4C illustrates a diagrammatic perspective view of the device, according to the present invention, in the second locked position with the Huber angled needle securely supported and contained therein;

FIG. 5 illustrates a diagrammatic perspective view of the device, according to the present invention, in the second locked position with the Huber angled needle contained therein;

FIG. 6A illustrates a diagrammatic front elevational view of a second embodiment of the device, according to the present invention, with a tactile indicator shown in a first position;

FIG. 6B illustrates a diagrammatic front elevational view of the second embodiment with the tactile indicator shown in a second position;

FIG. 7A illustrates a diagrammatic front elevational view of a third embodiment of the device, according to the present invention, sized to accommodate a coupling hub of a needle assembly;

FIG. 7B illustrates a diagrammatic right side elevational view of the third embodiment of FIG. 7A;

FIG. 7C illustrates a diagrammatic bottom plan view of the of slidable insert member of FIG. 7B;

FIGS. 9A through 9D are diagrammatic views of the fourth embodiment of the present invention which is capable of receiving the needle assembly of FIGS. 8A and 8B;

FIGS. 10A through 10D are diagrammatic views of the fourth embodiment showing removal of the needle assembly of FIGS. 8A and 8B;

FIGS. 13A and 13B are diagrammatic perspective views of an alternative embodiment of the device according to the present invention.

DETAILED DESCRIPTION OF THE INVENTION

Briefly described, the present device relates to the safe removal and containment of a needle, such as a Huber angled needle or Huber needle/syringe assembly. The device is an improvement over the prior art in that it is cost effective, easy to manipulate, and safe to use for both the patient and the care giver.

The following description is of a first embodiment and is in no way meant to limit the scope of the device in its size or shape, in its ability to be either manual or automatic operated, nor limited in the materials used in its construction or in the orientation of the components.

Figure 1:
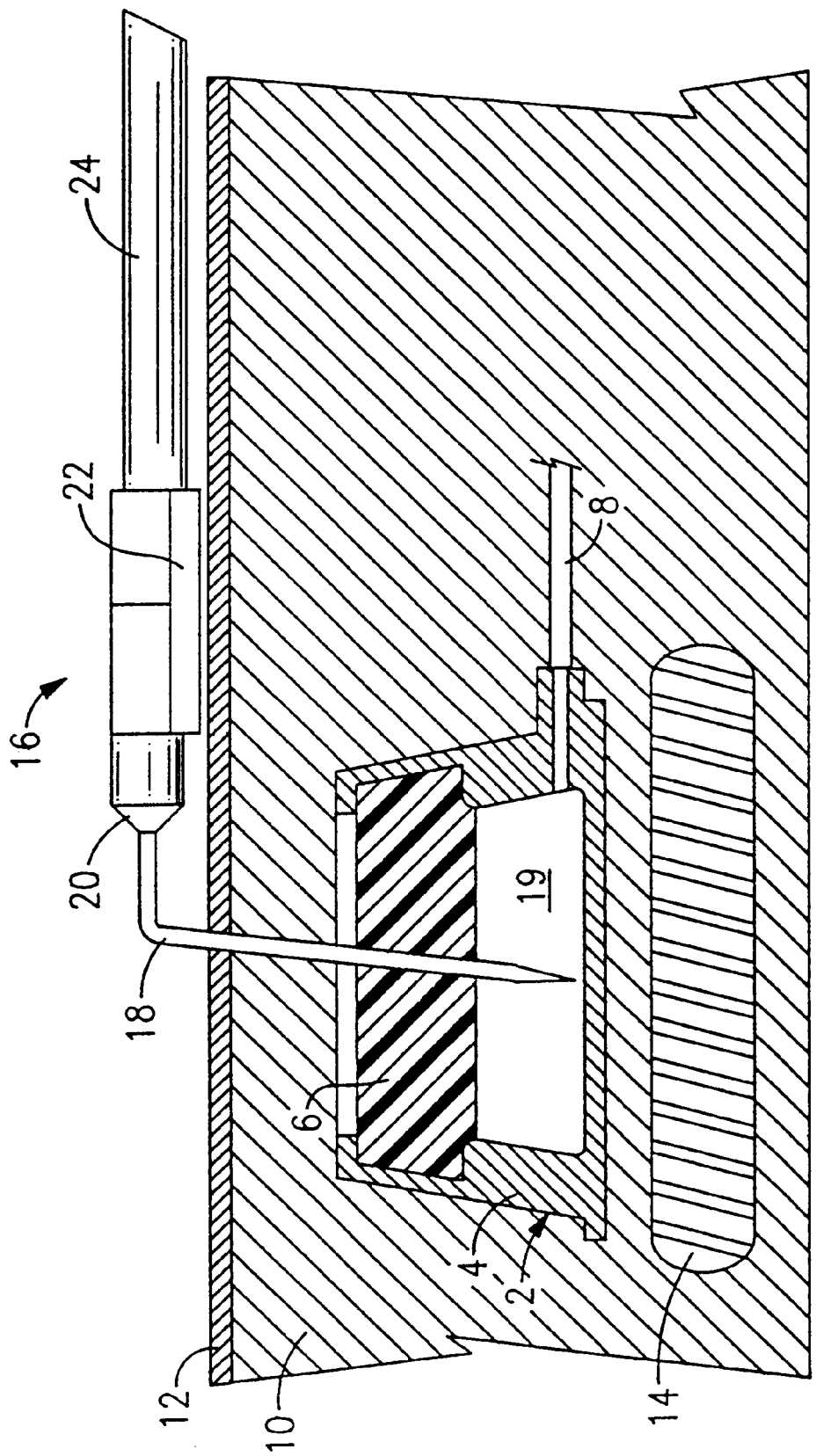
FIG. 1 illustrates a diagrammatic cross sectional view of a conventional Huber needle communicating with an implanted vascular port.

Referring first to FIG. 1, this Figure illustrates what is known in the prior art concerning use of Huber angled needle. FIG. 1 shows a diagrammatic cross sectional view of an implanted vascular port 2, constructed of a biocompatible metal housing 4 supporting an elastomeric septum 6, and coupled to a connecting catheter 8. The implanted vascular port 2 is shown positioned within the subcutaneous muscle 10, under the surface of the skin 12, and on top of a bone 14.

A Huber angled needle 16, is shown with the bent needle shaft 18 penetrating the surface of the skin 12, the subcutaneous muscle 10, and the elastomeric septum 6 into a chamber 19 of the implanted vascular port 2. The Huber angled needle 16 comprises the elongate bent needle shaft 18, a coupling hub 20, a pair of opposed handling/securing wings 22, an extension tube 24, and a female luer connector 26 (FIG. 5), which is not shown in this Figure.

With reference to FIGS. 2A through 4C, a detailed description concerning the present invention will now be provided.

The device 27 of the present invention comprises a wall defining an exterior housing 28. The exterior housing 28, in turn, defines an interior compartment 30 therein. The exterior housing 28 is provided with a pair of spaced apart fixed legs 32 (FIG. 2C), at a lower first end thereof, and is closed at the opposite second top end thereof. The spaced apart fixed legs 32 are separated from a remainder of the exterior housing 28 by a mouth 31. The pair of spaced apart fixed legs 32 are separated from one another by an elongate fixed leg slot 33 having a width greater than the diameter of the Huber needle 16 to be received therein. The purpose of the slot will be explained in further detail below.

An inner slidable member 36 is located within the interior compartment 30 of the exterior housing 28. The inner slidable member 36 comprises a main body portion 37 supporting a pair of spaced apart legs 38 which are separated from one another by an elongate movable leg slot 39 having a width slightly greater than the diameter of the Huber needle 16 to facilitate passage of the Huber needle 16 therebetween. The purpose of the elongate movable leg slot 39 will be explained in further detail below. In addition, the pair of spaced apart legs 38 are separated from the main body portion 37 of the inner slidable member 36 to define a needle removing cavity, area or surface 40 having a height greater than the diameter of the Huber needle 16 and the coupling hub 20 to facilitate receiving of the same therein. The purpose of the needle removing surface 40 surface will be explained in further detail below.

A pair of opposed side walls of the exterior housing 28 support a pair of opposed guide tracks or slots 42 which engage guide pins or tabs 44, or some other conventional guide member, supported by the inner slidable member 36, to guide and prevent tilting of the inner slidable member 36 as it moves within the interior compartment 30 of the exterior housing 28, and the purpose of such movement will be explained in further detail below. The locking tabs 44 extend through the guide slots 42 provided in the exterior housing 28 and are freely movable therealong. The end portions of the guide slots 42, located adjacent the closed end of the exterior housing 28, are each provided with a pair of inwardly facing locking protrusions 48 which allow passage of the locking tabs 44 thereby, in one direction, but prevent return passage of the locking tabs 44, in the opposite direction, to thereby permanently retain the locking tabs 44 adjacent the closed end of the exterior housing 28 once engaged therewith. By this arrangement, the locking tabs 44 permanently retain the inner slidable member 36 in a locked second position.

Figure 2A:
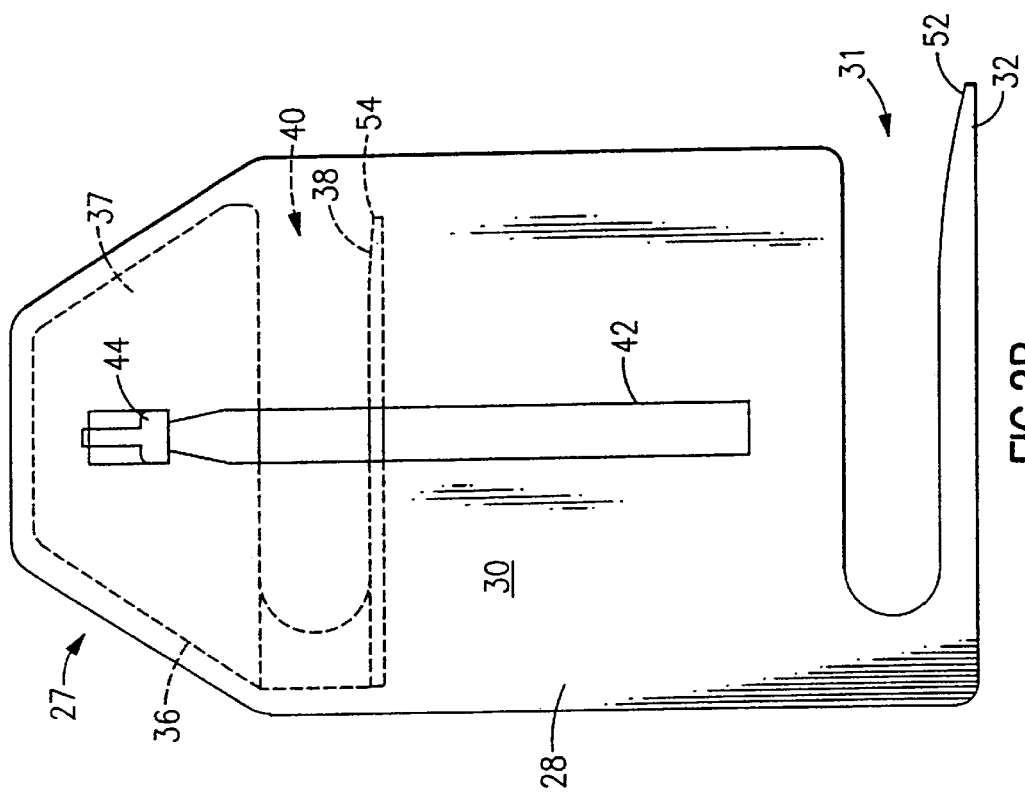
FIG. 2A illustrates a diagrammatic front elevated view of the device, according to the present invention, in an initial position with the slidable inner member shown in dashed lines.
Figure 2B:
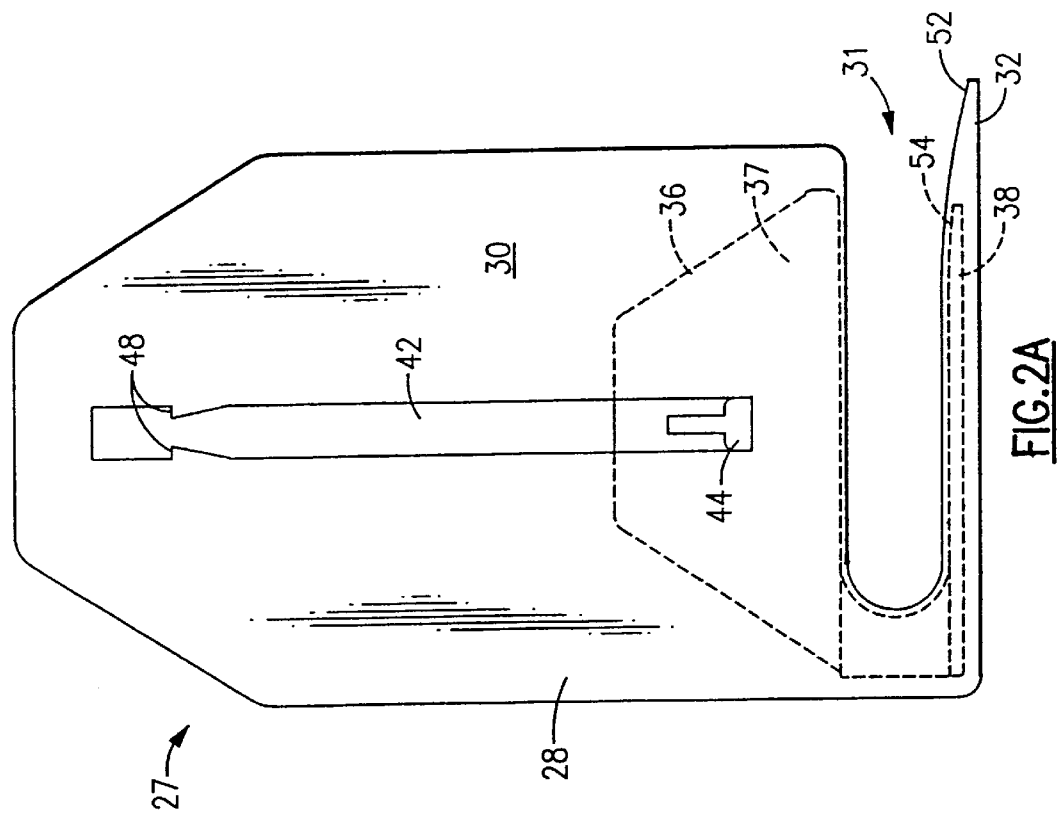
FIG. 2B illustrates a diagrammatic front elevated view of the device, according to the present invention, in a second locked position with the slidable inner member shown in dashed lines.

As can be seen in FIG. 2A, the inner slidable member 36 is shown in the first position with the spaced apart legs 38 located outside of the interior compartment 30 of the housing 28, e.g. adjacent the mouth 31, to facilitate engagement with the Huber needle and for retracting the needle when desired. Such retraction is achieve by moving the inner slidable member 36 from the first position (FIG. 2A) to the second retracted position (FIG. 2B) where the Huber needle 16 is completely retracted inside the exterior housing 28 of the device 27 to completely retract the needle and prevent an inadvertent needle stick.

With reference to FIGS. 4A–4C, use of the present invention to retract a needle will now be described. As can be seen in FIG. 4A, the pair spaced apart movable legs 38 are located, in this position, adjacent the mouth of the device 27. With the spaced apart movable legs 38 in this position, the bent portion of the needle 18 can be readily received by the elongate fixed leg slot 33 and the elongate movable leg slot 39 (FIG. 2C) formed between the pair of spaced apart fixed and movable legs 32, 38. As the device 27 is brought into engagement with the needle/assembly (FIG. 4B), the needle is initially received by the entrance of the elongate slot 39. To facilitate engagement therewith, the leading edge of the elongate fixed legs slot 33 of the fixed legs 32 is preferably provided with a V-shaped or chamfered entrance 58 (FIG. 2C), e.g. the entrance is wider than a remainder of the elongate slot 39.

Further relative movement between the device 27 and the needle/assembly, with the pair of spaced apart fixed legs 32 and the movable legs 38 being located between an undersurface of the needle and a top surface of the skin of the patient can occur until the bent end surface of the needle 16 abuts against or is located closely adjacent an end surface of the inner slidable member 36. Once such engagement occurs, the needle is properly positioned and safe retraction of the needle 16 can then occur. This is achieved by the care giver grasping the opposed pair of locking tabs 44 and moving them from the first position, shown in FIG. 4B, to the second retracted position, shown in FIG. 4C, whereby the locking tabs 44 are moved along the guide slot 42 past the locking protrusions 48 so as to permanently retain the inner slidable member 36 in the second position located within the housing. During movement of the locking tabs 44 along the housing slot 42, the inner slidable member 36 is guided along the guide slots 42 via the associated guide locking tabs 44.

The completely retracted position of the needle 16 can be seen in FIGS. 3 and 4C. Once the needle is completely retracted, the engagement between the locking tabs 44 and the locking protrusions 48 prevent return movement of the inner slidable member 36, from the second position to the first position, and maintains the needle housed completely within the exterior housing 28 whereby the needle can not readily "stick" another person. Thereafter, the female luer connector 26, attached to opposite end of the extension tube 24, can be disconnected from a desired supplied device 49 (FIG. 5) and connected to a male luer connector 50 supported by an outer surface of the exterior housing 28. This arrangement allows the removed male or female luer connector to be coupled to the exterior housing 28 to render the device slightly more compact for disposal purposes.

It is to be appreciated that the components of the device can be manufactured from plastic, metal or any other suitable material. Preferably at least one of the spaced apart movable legs 38 and/or the fixed legs 32 is tapered 52, 54, at a free end thereof, to facilitate locating the device 27 between an undersurface of the needle 16 and a top surface of the skin 12. Preferably the leading edge of at least the fixed leg slot 33 is provided with a V-shaped or chamfered entrance 58 (FIG. 2C) and possibly the leading edge of the elongate movable leg slot 39 may also be provided with a V-shaped or chamfered entrance to facilitate receipt of the needle 16 between the pair of legs. Lastly, a concave depression or section 60 can be provided in the top surface of the device 27 to facilitate the engagement of the device 27 by the hand of the user, e.g. typically the care giver will place his/her thumb on the concave section 60 and will locate his/her index and middle fingers, of the same hand, on the undersurface of the two opposed locking tabs 44. The index and middle fingers are then moved in a direction towards the thumb which moves the locking tabs 44 and, in turn, the inner slidable member 36 from its first to its second locked position whereby the Huber needle 16 is removed from the vascular port 2 and safely and completely retracted inside the device 27. Following the retraction of the Huber needle 16 into the device 27 and locking of the inner slidable member 16 in its second position, the entire device 27, including the Huber needle 16, can be disposed of into a biohazard sharps container.

It is to be appreciated that each of the fixed legs of the exterior housing 28 are provided with a recessed area 62 (FIG. 5) to facilitate receiving the movable legs 38 of the inner slidable member 36, which are typically shorter in length than the fixed legs 32. Further, movement of the inner slidable member 36 must be of sufficient distance to insure that the pointed tip 17 of the needle 16 is completely retracted inside the interior compartment 30 to prevent an inadvertent needle stick.

It is also to be appreciated that a variety of different known locking mechanisms can be utilized to lock the inner slidable member in the second position. As such other locking arrangements are well known to those skilled in this art, a further detailed description concerning the same is not provided herein.

An important aspect of the present invention is that the slidable member have a needle receiving area, surface, recess, or cavity for receiving, supporting, engaging or grasping a portion of the needle to be removed to facilitate removal of the needle from a patient. Further, said slidable member must be movable from a first position in which a least a portion of said needle receiving area, surface, recess, or cavity is located adjacent said mouth of said needle retraction device, for receiving the needle, to a second retracted position in which said needle receiving surface, along with a supported needle, are completely retracted inside said interior compartment of said exterior housing to prevent an inadvertent stick of the needle. As there are a variety of other possible arrangement for the slidable member which would be readily apparent to one skill in the art, a further detailed description concerning a few additional embodiments is provided below.

For example, a tactile indicator can be utilized with the device 27 of the present invention to provided a care giver with a positive indication that the inner slidably member is properly retracted and locked in its second position. As shown in FIGS. 6A and 6B, a top surface of the inner slidably member 36 is provided with a tactile indicator button 100 and a mating aperture 102 is formed in the exterior housing 28, adjacent the closed end 98 thereof. The tactile indicator button 100 and the mating aperture 102 are axially aligned with one another to facilitate proper engagement.

When the inner slide member 36 is moved from its first position, illustrated by FIG. 6A, to its second position, illustrated by FIG. 6B, to a position where the guide tabs 44 are locked in place by the inwardly facing locking protrusions 48, the indicator button 100 protrudes a sufficient distance through the mating aperture 102 and can be viewed and/or physically sensed by the thumb, for example, of the care giver. Due to this arrangement, the inner slide member 36 must be fully retract before the care giver is able to sense the tactile indicator button 100 projecting through the mating aperture 102. It is to be appreciated that the tactile indicator button 100 is sized and/or formed on the top surface 96 of the inner slide member 36 such that the button 100 can only be viewed or felt by a finger of a care giver when the inner slide member 36 is properly locked in the second position.

Alternatively, the inner slide member 36 can be modified to receive Huber needles of various designs. As seen in FIGS. 7A and 7B, for example, a third embodiment of the present invention is shown. According to this embodiment, the inner slide member 36 is modified such that the device 27, according to the present invention, may readily accommodate a conventional needle assembly 104, commonly known as "The Gripper(™)". The basic components of the needle assembly 104 are depicted in FIGS. 8A and 8B and will be briefly described below.

Figure 8B:
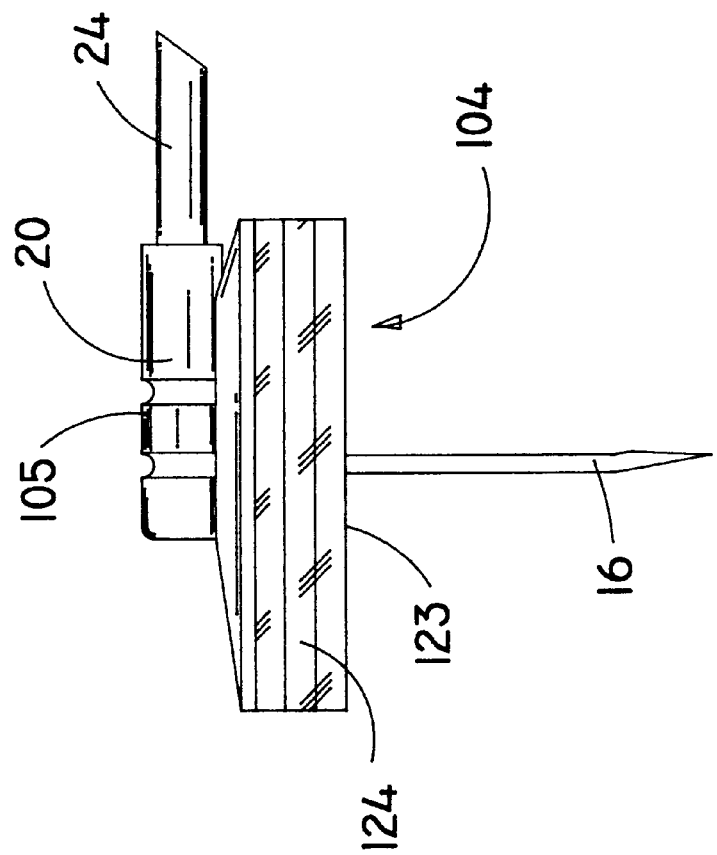
FIG. 8B illustrates a diagrammatic right side elevational view of the prior art needle assembly of FIG. 8A.
Figure 8A:
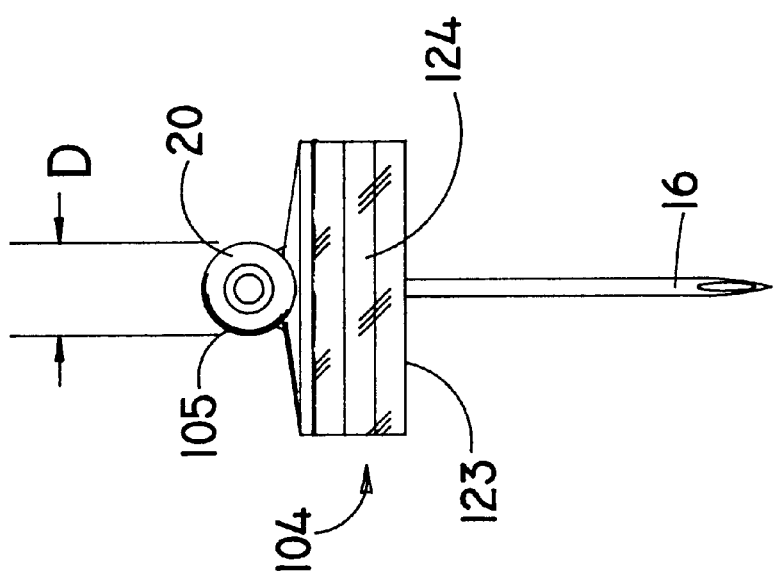
FIG. 8A illustrates a diagrammatic front elevational view of a prior art needle assembly.

With reference to FIGS. 8A and 8B, a brief description concerning the prior art "The Gripper(™)" needle assembly 104 will now be provided. As with the previous embodiments, this prior art design has a Huber needle 16 which is connected to a coupling hub 20. A remote free end of the coupling hub 20, in turn, is connected to an extension tube 24 while the opposite end of the extension tube may be connected to a female luer connector (not shown in this Figure) as with the previous embodiments. The coupling hub 20 is cylindrical in shape (FIG. 8A) and has a diameter D which is typically about 3/16 of an inch. The coupling hub 20 is formed integrally with a base 124. The base 124, being made of foam, has a flat planar bottom surface 123, which is generally rectangular in shape, for facilitating mating engagement with a planar top surface of the skin of a patient. Preferably the needle assembly 104 has a short or shallow height to facilitate unintrusive use of the device by a patient.

According to this third embodiment, a pair of spaced apart shoulders 138 are separated from one another by an elongate slot 39. The pair of shoulders 138 are spaced from one another and contoured along with an inwardly facing surface of a remaining portion of a main body portion 37 of the inner slide member 36 to form a needle removing cavity 40. The needle removing cavity 40 is generally semi-cylindrical in shape (FIG. 7B) and is sized to closely receive and accommodate the cylindrical exterior surface 105 (FIG. 8A) of the coupling hub 20 therein. One end surface of the main body portion 37 is provided with an opening 106 to facilitate receiving the coupling hub 20 within the needle removing cavity 40 while a stop end wall 107 is provided in the opposite end of the main body portion 37 to prevent over-insertion of the coupling hub 20 within the needle removing cavity 40. The inner slide member 36 is able to receive the coupling hub 20 of the needle assembly 104 (FIG. 8A) when the coupling hub 20 is axially aligned with the opening 106 of the needle removing cavity 40 and moved relative thereto.

An edge portion of a side wall of the exterior housing 28, located adjacent the opening 106 provided in the main body portion 37, can be provided with a V-shaped or concave shaped notch 108. The notch 108 facilitates easier retraction of the needle assembly 104 into the exterior housing 28 by providing a receiving and bending or fold area for the extension tube 24 as the inner slide member 36 is moved from its first position (FIG. 7D) to its second fully retracted and locked position (FIG. 7F).

It is to be appreciated that the distance d (FIG. 7B) separating the spaced apart shoulders 138 from one another is less than the diameter D of the outer cylindrical surface 105 of the needle assembly 104 (see FIG. 8A) to facilitate captive retaining of the needle assembly 104 once the coupling hub 20 is received by the needle removing cavity 40 of the inner slide member 36. As with the two previous embodiments, a pair of opposed side walls of the exterior housing 28 support a pair of opposed guide tracks or slots 42 which engage guide pins or tabs 44 supported by the inner slide member 36. Activation of the guide tabs 44, along the guide slots 42, move the inner slide member 36 therealong from its initial position (FIG. 7D) to its retracted position (FIG. 7F).

Figure 7D:
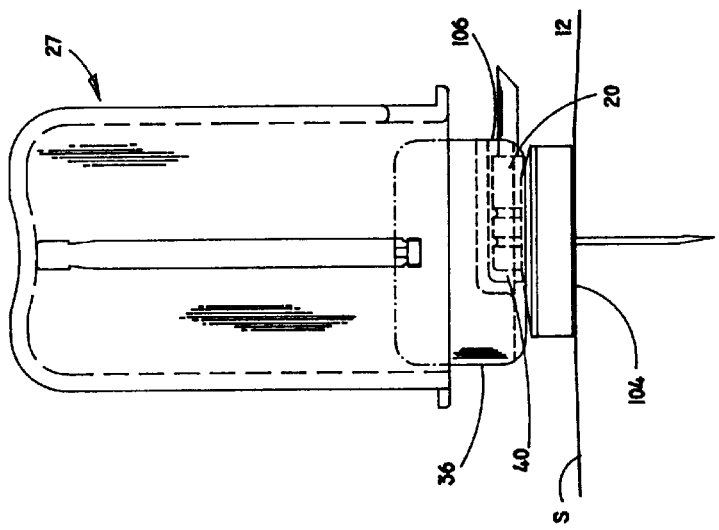
FIGS. 7D through 7F are diagrammatic views which illustrate operation of the third embodiment of the invention.
Figure 7E:
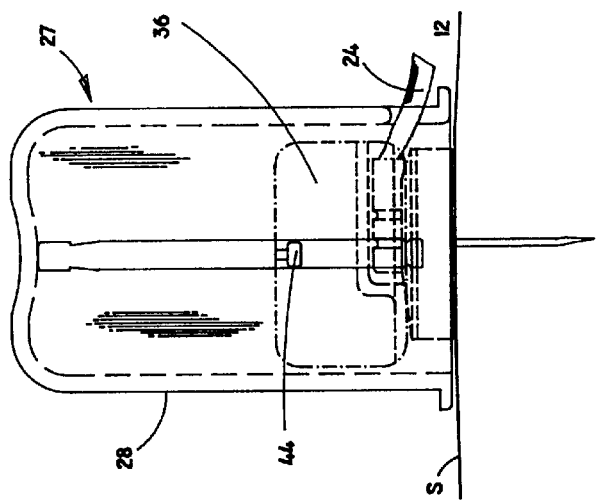
Figure 7F:
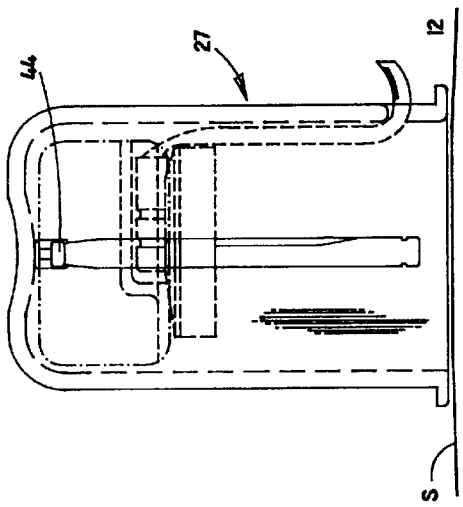

As depicted in FIG. 7D, after the device 27 of the present invention has been brought into engagement with the needle assembly 104 but prior to sliding movement of the inner slide member, e.g. the coupling hub 20 passes through the opening 106 and is received within the needle removing cavity 40, the pair of spaced apart shoulder 138 (FIG. 7B) retain the coupling hub 20 within the needle retaining cavity 40. With the coupling hub 20 sufficiently supported by the inner slide member 36, the needle assembly 104 can then be retracted into the device 27 by moving or biasing the exterior housing 28 toward and into contact with a surface S of the patient's skin 12 (FIG. 7E) and thereafter retracting the inner slide member 36, via actuation of the guide tabs 44, until the inner slide member 36 is completely retracted within the exterior housing 28 and is locked in its second position (FIG. 7F), in the same fashion as previously described above.

With reference to FIGS. 9A and 9B, a fourth embodiment of the present invention, somewhat similar to the third embodiment, will now be described. According to this embodiment, the inner slide member 36 has a main body portion 37 but is a completely separate and independent component from the exterior housing 28. According to this embodiment, the inner slide member 36 has a longitudinal length E. The inner slide member 36 is generally rectangular in shape and also has a generally transverse rectangular cross section. A first end of the main body portion 37 supports a pair of shoulders 138 spaced from one another and contoured, with a remaining portion of a main body portion 37 of the inner slide member 36, to form a needle removing cavity 40. As with the previous embodiment, the needle removing cavity 40 is semi-cylindrical in shape (see FIGS. 9B and 9D) and is sized to closely receive and accommodate therein the cylindrical exterior surface 105 (FIG. 8A) of the coupling hub 20. An opening 106 is provided adjacent one end of the main body portion 37, to facilitate receiving the coupling hub 20 within the needle removing cavity 40 while a stop end wall 107 is provided, in the opposite end of the main body portion 37, to prevent over-insertion of the coupling hub 20 in the needle removing cavity 40. The opposite end of the elongate body portion 37 supports a pair of opposed, fixed guide tabs 44. As these elements are substantially identical in function to the previously discussed elements, a further detail discussion concerning the same is not provided.

An exterior surface of the main body portion 37 of the inner slide member 36, adjacent the end supporting the needle removing cavity 40, is provided with an elongate transversely extending recess 110. The recess 110 is spaced a distance L from an under surface 111 of the guide tabs 44. This recess 110 extends the entire width of the slide member 36 and is sized to mate with an associated spring latch 112 of the housing. The associated spring latch 112 is integrally formed in a side wall of the exterior housing 28 of the device 27 (FIG. 9C), and a further detail discussion concerning the purpose of the same will follow hereafter.

The exterior housing 28 of the device (FIG. 9C) has a longitudinal length I which is either equal to or slightly less than the recess spacing distance L. As shown in FIG. 9C, distance L is approximately equal to the length I of the exterior housing 28 such that when the inner slide member 36 is inserted and received within the through bore of the exterior housing 28, during assembly (see FIG. 9D) of the device 27, the exterior housing 28 encloses and covers the recess 110 thereby forming a nested arrangement between those two components.

During assembly, the first end of the inner slide member 36 is received and inserted through a top opening 114 provided in the exterior housing 28 opposite the mouth 31. During such insertion, the inner slide member 36 is moved relative to the exterior housing 28 until the under surface 111 of the guide tabs 44, formed integral with the inner slide member 36, abuts against a top edge 115 of the exterior housing 28. Such abutting engagement acts as a stop and prevents further relative movement between the inner slide member 36 and the exterior housing 28 to thereby prevent insertion of the inner slide member 36 beyond the position shown in FIG. 9D. A remote end of the guide tabs 44 preferably extends outwardly away from the exterior housing 28 a sufficient distance to facilitate actuation of the guide tabs 44, when desired.

The elongate inner slide member 36 has transverse dimensions (e.g. a length and a width) which are slightly smaller than the transverse dimension(s) of the through bore of the exterior housing 28 to facilitate relative sliding movement therebetween. It is to be appreciated that the transverse shape of the inner slide member 36 can vary, from application to application, but is always sized slightly smaller than the transverse dimensions of the through bore provided in the exterior housing 28 to facilitate the desired engagement. The elongate inner slide member 36 also has outwardly facing bearing surfaces 116 which mate with the inwardly facing bearing surfaces, formed within the through bore of the exterior housing 28, to facilitate the desired relative sliding movement while also minimizing any axial play between those components.

It is to be appreciated that the total longitudinal length E of the elongated inner slide member 36 must be such that at least the opening 106 of the cavity 40 of the inner slide member 36 is fully exposed, past a lower edge 113 of the exterior housing 28, following completion of insertion of the inner slide member 36 within the exterior housing 28 during the assembly phase.

Figure 10D:
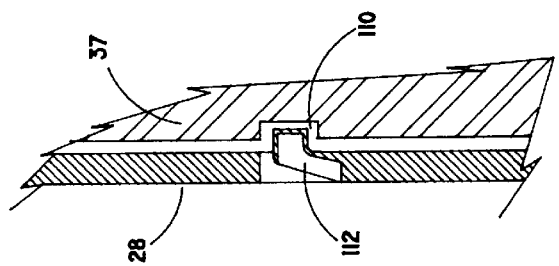

As shown in FIG. 9C, the spring latch 112 is provided in a side wall of the exterior housing 28 and spaced a distance H from the mouth 31 of the device 27. It is to be appreciated that the distance H is such that when the inner slide member is moved from its first extended position to its second fully retracted position, depicted by FIG. 10C, the spring latch 112 is allowed to expand and be biased into engagement with the recess 110 of the inner slide member (FIG. 10D). The engagement between the spring latch 112 and the recess 110 acts as a stop and prevents the further relative movement of the inner slide member 36 with respect to the exterior housing 28 thereby locking the needle assembly 104 safely inside the interior compartment of the device 27. The spring latch 112 must not be placed too close to the top opening 114 of the exterior housing 28 so as to allow the inner slide member 36 to become inadvertently disconnected from the exterior housing 28. As this embodiment is not provided with any guide slots or other side openings in the exterior housing 28, this arrangement further decreases the possibility of an inadvertent needle stick to care giver, a patient or another individual.

FIG. 9D shows the device as assembled with the inner slide member 36 inserted and moved to its first position. A concave notch 108, which functions similarly to the previously discussed notch, is provided in the exterior housing 28 adjacent the mouth 31 and a further detail discussion concerning the same is not provided. As can been seen from this Figure, when the inner slide member 36 is in its first position, with guide tabs 44 abutting against the top edge 115 of the exterior housing 28, the opening 106 of the cavity 40 is fully exposed and ready to receive the a mating portion of the needle assembly 104, when necessary, as with the third embodiment.

Figure 10C:
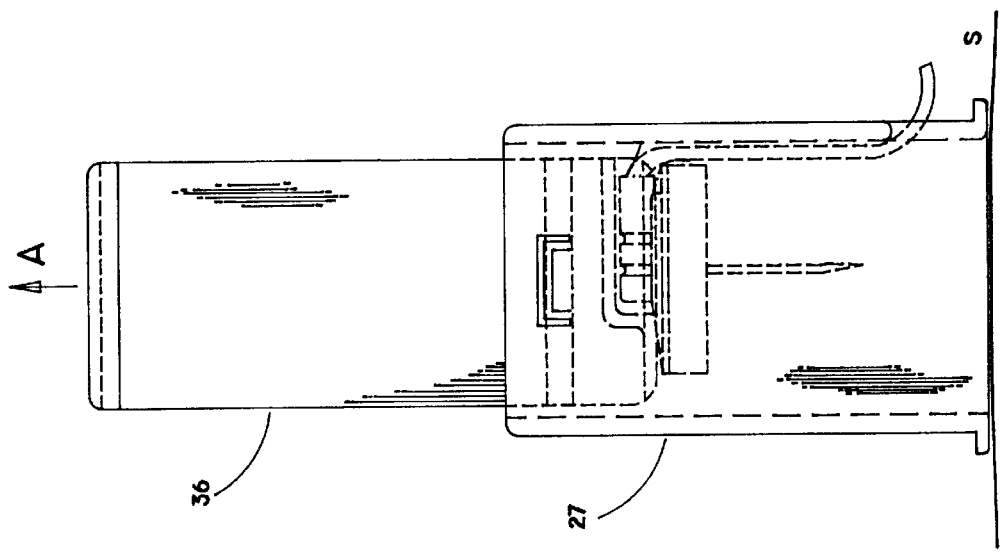

FIGS. 10A, 10B and 10C, illustrate the procedure for utilization of the fourth embodiment of the present invention. When use of the device 27 is desired, the care giver slides a coupling hub 20 of a needle assembly 104, of the kind depicted in FIG. 8A, into the needle removing cavity 40 of the device 27, via the opening 106 of the inner slide member 36. Once the coupling hub 20 of the needle assembly 104 is captive received within the cavity 40, the device operates much like a syringe. The care giver, while holding or grasping the guide tabs 44, in one hand, grabs the exterior housing 28 with the other hand and moves the exterior housing 28 toward and into contact with a patient's skin S and steadies the device 27 with the aid of a peripheral lip 118 formed adjacent to the mouth 31 of the exterior housing 28 (FIG. 10B). With the device suitably steadied, the care giver then moves the elongate inner slide member 36 relative to the exterior housing 28, i.e. in the direction of arrow A, so as to commence withdrawal and/or removal of the elongate inner slide member 36 from the exterior housing 28. The inner slide member 36 is pulled in a removal direction, via the guide tabs 44, until the spring latch 112 engages with the recess 110 (FIG. 10D) and locks the inner slide member 36 in its second locked position (FIG. 10C).

As shown by FIG. 10D the spring latch 112 sufficiently engages with the recess 110 of the inner slide member to prevent any further movement, i.e. either a retraction or a reinsertion motion of the inner slide member 36 relative to the exterior housing 28, thereby retaining the retracted needle safely within the device 27.

Figure 11:
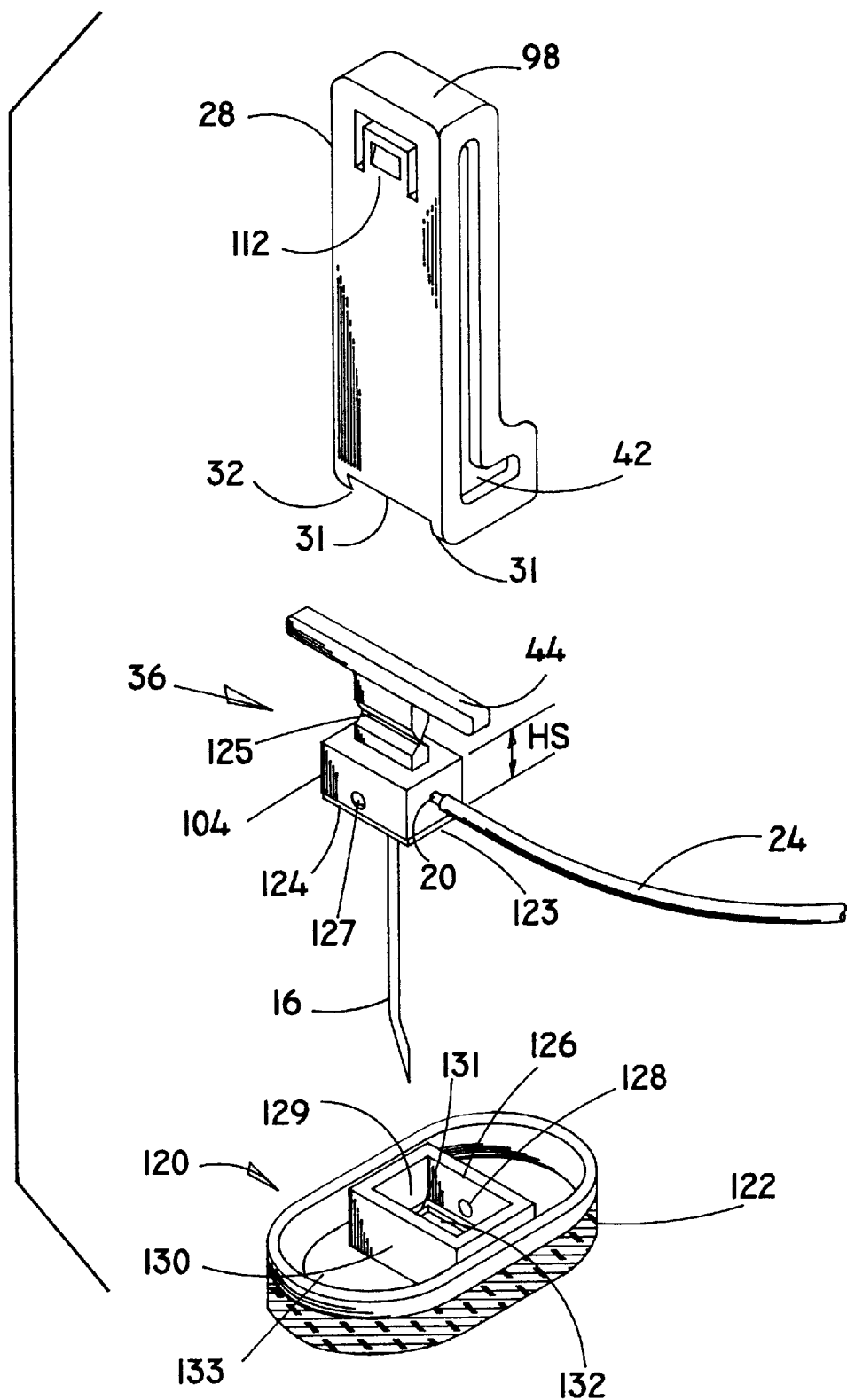
FIG. 11 is an exploded diagrammatic view of a fifth embodiment of the showing the exterior housing, the inner slide member, and the base.
Figure 12A:
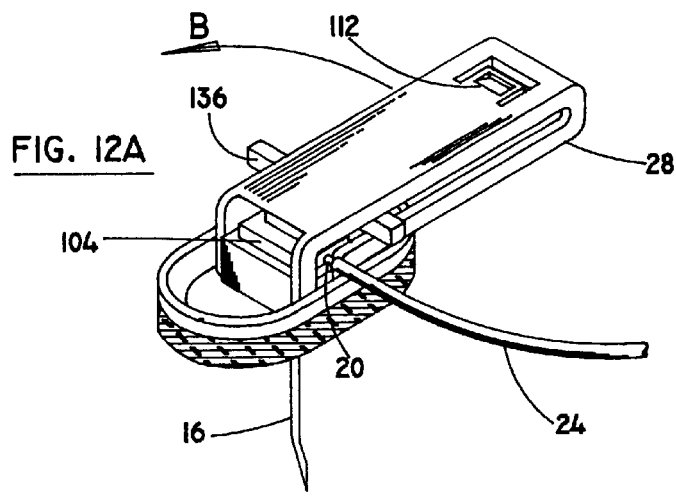
FIGS. 12A through 12D illustrate the use of the device show in FIG. 11.

Turning now to FIG. 11, a fifth embodiment of the present invention is shown. According to this embodiment, the exterior housing 28 is provided with a pair of opposed guide slots 42 and a spring latch 112 is formed adjacent a closed end 98 of the exterior housing 28, as with the previous embodiments. The exterior housing 28 is closed at one end 98 and has a mouth 31 formed at the opposite end thereof. The inner slide member 36 comprises a unitary needle assembly 104 which supports a Huber needle 16. The needle base 124 is generally rectangular in shape and has a flat planar surface 123 for engagement with a top surface of the skin of a patient. The Huber needle 16 is preferably molded integrally with the needle base 124 and the opposite end of the Huber needle 16 is connected to a coupling hub 20. A remote free end of the coupling hub 20, in turn, is connected to an extension tube 24 for supplying the desired product to the patient. A pair of guide tabs 44, which are sized and shaped to mate with the guide slots 42 of the exterior housing 28, are pivotally attached to a centrally top area of the needle base 124. The guide tabs 44 are hingedly connected to the base 124 via a living hinge 125 located therebetween. The living hinge 125 allows the guide tabs 44 to pivot from an upright position (see FIG. 11) to a bent over or supine position (see FIG. 12A), and vice versa, to facilitate both use and retraction of the needle assembly 104.

The needle assembly 104 is releasably engaged with an assembly base 120. The assembly base 120 is provided with a centrally located assembly recess 126 which is shaped and sized to intimately receive the needle assembly 104 therein. As can be seen in FIG. 11, the assembly recess 126 is generally rectangular in shape and intimately receives and retains the rectangular needle base 124. To provide such releasable engagement, at least one pair of opposed outwardly facing surfaces of the needle assembly 104 are each provided with at least one protrusion(s) or detent(s) 127 which is located to engage with at least one mating indentation(s) 128 provided in a pair of opposed side walls defining the assembly recess 126. A perimeter rim 131 is provided at a bottom of the assembly recess 126 to support and prevent over insertion of the needle assembly 104 into the assembly recess 126 of the assembly base 120. A bottom surface of the assembly base 120 is preferably planar and may be provided with a cushion adhesive 122 which directly contacts the skin of the patient during use, to facilitate an efficient and comfortable securing of the device to the patient. The perimeter rim 131 ensures that the planar surface 123 of the needle base 124 are substantially coplanar with the bottom surface of the assembly base 120 during use. During initial assembly, the needle assembly 104 is at least partially housed within the exterior housing 28 such that each one of the guide tabs 44 engages with one of the guide slots 42 to facilitate the sliding motion of the guide tabs 44 relative to the guide slots 42. Once this has occurred, the use of the device 27, according to this embodiment, can then occur.

Prior to use, the needle assembly 104 is coupled to a desired assembly base 120 by receiving the needle assembly 104 within the assembly recess 126. It is to be appreciated that the Huber needle 16 extends through a mating aperture 132 provided in a bottom of the assembly base 120 as well as an aperture (not shown) in a bottom of the cushion adhesive 122. Thereafter, the Huber needle 16 is brought into engagement with a desired location on the skin of a patient, to engage with an implanted septum, and following engagement with the implanted septum generally secured thereto by the cushion adhesive surface 122. If necessary, additional tape or other conventional securing mechanisms can be utilized to securely position the device 27, during use (see FIG. 12A), to maintain the exterior housing 28 in a position extending parallel to the skin of the patient and located adjacent thereto. Once the desired treatment has been achieved, and removal of the device 27 is desired, the exterior housing 28 is rotated 90 degrees, via the living hinge 125, in the direction of arrow B, away form the skin from the supine position to the upright position shown in FIG. 12B. The living hinge 125 facilitates such pivoting motion without disrupting the position of the embedded needle assembly 104.

Figure 12B:
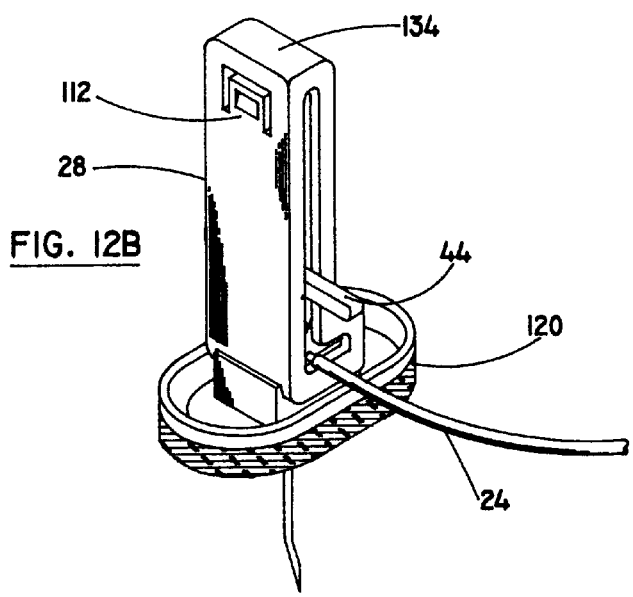
Figure 12C:
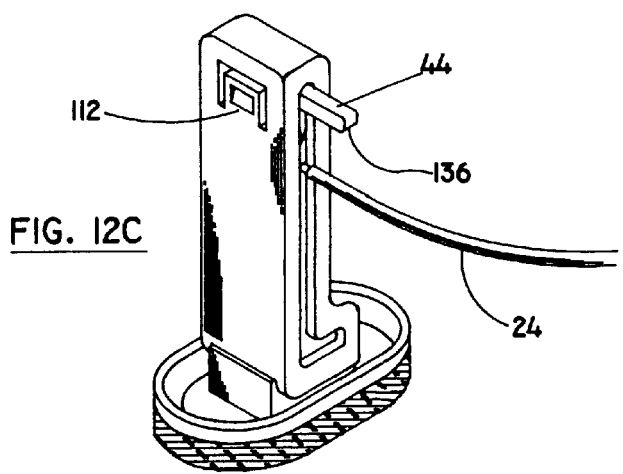

With the exterior housing 28 in this upright position, the care giver grasps the device 27 both by placing a thumb or his/her palm on a top end surface 98 of the exterior housing 28 and curls an index finger around one of the guide tabs 44 and a middle finger around the other one of the guide tabs 44. Once the guide tabs 44 are appropriately grasped, the device 27 can further be steadied by the care giver placing the index and middle fingers, of the other hand, on the assembly base 120. Finally, the care giver commences biasing of the guide tabs 44 away from the assembly base 120 to unseat the inner slide member 36 from the assembly base 120, e.g. the detents 127 disengage from the mating indentations 128. Continued sliding movement the guide tabs 44, away from the assembly base 120 toward the closed end of the exterior housing 28, occurs until the guide tabs 44 abut against an end of the guide slots 42 and the Huber needle 16 is thus fully retracted and locked in the second position, depicted by FIG. 12C. It is to be appreciated that the needle assembly 124 must have a sufficient height HS to space the exterior housing 28 away from an upwardly facing surface lip 133 of the assembly base 120 to allow the desired pivoting motion of the exterior housing 28. This height spacing HS prevents interference from the assembly base 120 during the pivoting motion of the exterior housing 28 from its supine position (see FIG. 12A) to its upright position (FIG. 12B).

Figure 12D:
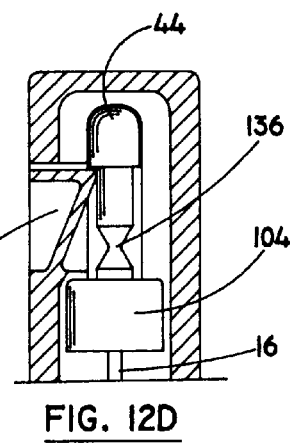

The Huber needle 16 is locked in the second position by the spring latch 112 engaging with a bottom surface or ridge 136 of the guide tabs 44, as illustrated by FIG. 12D. With the needle fully retracted and locked in the second position, inadvertent stick of the needle to the care giver is thus minimized and/or prevented.

With reference to FIGS. 13A and 13B, a sixth embodiment of the device of the present invention will now be discussed. It is to be appreciate that the device 27, of this embodiment, is similar to the device shown in FIG. 10A. The major difference of this embodiment being the modifications made to the inner slide member 36. As the exterior housing 28, with its spring latch 112 and interior bearing surface 116, are essentially the same features as those described in FIG. 9C, a further detail discussion concerning the same is not provided.

As can be seen in FIG. 13B, a remote end of the needle 16 is coupled to a first end of an extension tube 24. According to this embodiment, the extension tube 24 is substantially axially aligned with the pointed end portion of the Huber needle 16 instead of being at a right angle therewith, as with the previous embodiments. In order to facilitate this engagement, the Huber needle 16 must be securely embedded within the needle assembly 104 to allow both insertion and removal of the needle, as desired, without the needle separating from the needle assembly 104. In addition, the extension tube 24 extends through the inner slidable member 36 from an inlet 138 provided at opposed ends of the main body portion 37. Furthermore, the extension tube 24 is part of the living hinge 125 so as to allow the exterior housing 28 to pivot from its use supine position (e.g. a position similar to that shown in FIG. 12A) to an upright retraction position (e.g. a position similar to that shown in FIG. 13A). It is to be appreciated that in this embodiment the length L of the inner slidable member 36 is greater than the length I of the exterior housing 28 by an amount to provided the inner slidable member 36 with a grasping length GL.

As with the embodiment of FIG. 10, when retraction of the needle assembly 104 is desired, the care giver, while holding the inner slidable member 36 in one hand along length GL, grasps the exterior housing 28, with the other hand, and moves the exterior housing 28 toward or into contact with a patent's skin while steadying the device 27 with the aid of the peripheral lip 118. It is to be appreciated that a thumb tab 140, as shown, is provided in the grasping length GL of the inner slidable member 36 to give the care giver a better surface to grasp, but however, the end of the inner slidable member 36 could easily be modified with a guide tab 44 as shown by FIG. 10, or a circular pull ring (not shown) or nothing at all, if desirable. With the device suitably steadied, the care giver than moves the elongate inner slidable member 36, relative to the exterior housing 28, to commence withdrawal or removal of the elongate inner slidable member into the exterior housing 28. The spring latch 112 engages with a recess, not shown in detail in this Figure, to lock the inner slidable member 36 relative to the exterior housing 28. As the extension tube 24 is not located between and exterior surface of the inner slide member 26 and an inwardly facing surface of the housing 28, the inner slide member 36, can have a very close tolerance or small clearance with a through bore of the exterior housing 28 and guide slots are not necessary in this embodiment. It is to be appreciated that the retraction of the needle assembly from the needle base also functions to completely separate the exterior housing 28 from the needle base 120.

Since certain changes may be made in the above described device and method, without departing from the spirit and scope of the invention herein involved, it is intended that all of the subject matter of the above description or shown in the accompanying drawings shall be interpreted merely as examples illustrating the inventive concept herein and shall not be construed as limiting the invention.

Wherefore, I claim:

1. A needle retraction device for removing a needle from a patient, said needle retraction device comprising:
   an exterior housing defining an interior compartment and being partially opened at least one end thereof, and the at least one partially opened end defining a needle receiving mouth;
   a moveable member supporting a needle retraction mechanism adjacent one end of said moveable member; and
   said moveable member being movable from a first position in which at least a portion of said needle retraction mechanism is located to engage with a needle, to a second retracted position in which said needle is completely retracted inside said interior compartment of said exterior housing, via said needle retraction mechanism, to prevent an inadvertent stick of the needle.

2. A needle retraction device according to claim 1, wherein said moveable member is provided with an indicator button, a closed end of said exterior housing is provided with a mating aperture which is axially aligned with said indicator button, and said indicator button engages with said mating aperture when said moveable member is moved, via at least one tab fixedly attached thereto, to its second retracted position to provide a positive indication thereof.

3. A needle retraction device according to claim 1, wherein said moveable member has at least one tab fixedly attached thereto, and the needle engagement mechanism comprises a needle removing cavity being formed adjacent one end of said inner moveable member, said needle removing cavity includes a pair of shoulders which are spaced apart from one another by an elongate slot, and a lateral opening provided access to said needle removing cavity.

4. The needle retraction device according to claim 3, wherein said at least one tab is pair of opposed tabs.

5. A needle retraction device according to claim 4, wherein said exterior housing, adjacent an opening of said needle removing cavity, is provided with a notch for engagement with an extension tube affixed to a needle during retraction of the needle.

6. The needle retraction device according to claim 3, wherein said exterior housing includes a locking mechanism which cooperates with said at least one tab supported by said moveable member for locking said moveable member in said second position.

7. The needle retraction device according to claim 3, wherein said needle is supported by a needle assembly which comprises an needle base supporting a Huber needle and a hub coupling and said hub coupling is engagable with said needle removing cavity.

8. The needle retraction device according to claim 1 wherein said exterior housing is open at two opposed ends thereof and has a through bore extending therethrough, and said moveable member is longer than said exterior housing so as to extend completely through both opposed open ends of said exterior housing and expose said needle retraction mechanism to facilitate retraction of a needle via said needle retraction mechanism.

9. The needle retraction device according to claim 8, wherein said needle retraction mechanism is supported adjacent one end of said moveable member and a pair of opposed tabs are fixedly attached adjacent the other end of said moveable member to facilitate retraction of said moveable member.

10. A needle retraction device according to claim 8, wherein the needle engagement mechanism comprises a needle removing cavity being formed adjacent one end of said inner moveable member, said needle removing cavity includes a pair of shoulders which are spaced apart from one another by an elongate slot, and a lateral opening provided access to said needle removing cavity.

11. A needle retraction device according to claim 10, wherein said exterior housing, adjacent an opening of said needle removing cavity, is provided with a notch for engagement with an extension tube affixed to a needle during retraction of the needle.

12. A needle retraction device according to claim 10, wherein a surface of said moveable member, adjacent the opening of said needle removing cavity, is provided with a transverse recess and an opposed end of said exterior housing is provided with a spring latch for engagement with said transverse recess once said moveable member is moved sufficiently with respect to said exterior housing during needle retraction.

13. The needle retraction device according to claim 1, wherein said moveable member has a hinge which facilitates moving said exterior housing from a supine position to an upright position, and vice-versa.

14. The needle retraction device according to claim 13, wherein said moveable member supports a needle assembly which comprises an assembly base supporting a needle and a hub coupling.

15. A needle retraction device according to claim 13, wherein said hinge of the moveable member is a pair of tabs hinged to a top surface of said moveable member, and a pair of opposed exterior walls of said housing are each provided with an elongate guide slot for each guiding one of said pair of hinged tabs, and each guide slot is provided with a locking mechanism for locking retaining said hinged tab when engaged therewith.

16. A needle retraction device according to claim 13, wherein the needle assembly is releasably engagable with an assembly base, having an aperture therein, via a pair of mating components, and said assembly base is releasably secured to skin of a patient during use.

17. A needle retraction device according to claim 8, wherein said pair of tabs hinged to the top surface of said moveable member facilitate pivoting motion of said exterior housing from an in use supine position to an upright retraction position, and vice-versa.

18. A needle retraction device according to claim 15, wherein each of said pair of tabs hinged to a top surface of said moveable member is provided with a bottom surface, and a portion of said exterior housing, adjacent a closed end thereof, is provided with a spring latch for engagement with said bottom surface of said pair of tabs hinged to a top surface of said moveable member once said pair of tabs hinged to a top surface of said moveable member are moved sufficiently with respect to said exterior housing during needle retraction.

19. A method of removing a needle from a patient with a needle retraction device, said method comprising the steps of:

defining, via an exterior housing, an interior compartment being partially opened at least one end thereof, and the at least one partially opened end defining a needle receiving mouth;

supporting a needle retraction mechanism adjacent one end of a moveable member; and arranging said moveable member to be movable from a first position in which at least a portion of said needle retraction mechanism is located to engage with one of a needle and needle assembly, to a second retracted position in which said one of said needle and needle assembly is completely retracted inside said interior compartment of said exterior housing, via said needle retraction mechanism, to prevent an inadvertent stick of the needle.

\* \* \* \* \*